United States Patent [19]

Seiler et al.

[11] Patent Number: 5,208,359

[45] Date of Patent: May 4, 1993

[54] PROCESS FOR THE PREPARATION OF DI-TERT.BUTOXYDIACETOXYSILANE

[75] Inventors: Claus-Dietrich Seiler; Hartwig Rauleder; Hans-Joachim Kötzsch; Reinhold Schork, all of Rheinfelden, Fed. Rep. of Germany

[73] Assignee: Huels Aktiengesellschaft, Marl, Fed. Rep. of Germany

[21] Appl. No.: 812,586

[22] Filed: Dec. 20, 1991

Related U.S. Application Data

[63] Continuation-in-part of Ser. No. 709,592, Jun. 3, 1991, abandoned.

[30] Foreign Application Priority Data

Jul. 9, 1990 [DE] Fed. Rep. of Germany ....... 4021870

[51] Int. Cl.⁵ ............................. C07F 7/08; C07F 7/18
[52] U.S. Cl. .................................................... 556/442

[58] Field of Search .......................................... 556/442

[56] References Cited

U.S. PATENT DOCUMENTS

| | | | |
|---|---|---|---|
| 2,986,875 | 6/1961 | Di Giorgio | 60/35.4 |
| 3,296,195 | 1/1967 | Goosseus | 556/442 X |
| 3,886,118 | 5/1975 | Nitzsche et al. | 556/442 X |
| 4,623,693 | 11/1986 | Inoue et al. | 524/700 |

OTHER PUBLICATIONS

Chemical Abstracts, vol. 52, 1958, Abstract No. 36731.

Primary Examiner—Paul F. Shaver
Attorney, Agent, or Firm—Felfe & Lynch

[57] ABSTRACT

Di-tert.butoxydiacetoxysilane is prepared by reacting tetraacetoxysilane with tert.butanol at a reaction temperature of up to 60° C., and the resulting di-tert.butoxydiacetoxysilane is isolated.

4 Claims, No Drawings

PROCESS FOR THE PREPARATION OF DI-TERT.BUTOXYDIACETOXYSILANE

This is a continuation-in-part of co-pending application Ser. No. 07/709,592, filed Jun. 3, 1991, now abandoned.

FIELD OF THE INVENTION

The present invention relates to a novel process for the preparation of di-tert.butoxydiacetoxysilane from tetraacetoxysilane and tert.butanol.

BACKGROUND OF THE INVENTION

Di-tert.butoxydiacetoxysilane is useful especially as a cross-linking agent for the preparation of compositions which have a long shelf life under exclusion of moisture and are curable at room temperature on contact with moisture to form elastomers. Such compositions are obtained by admixing diorganopolysiloxanes containing condensable terminal groups with crosslinking silicon compounds.

U.S. Pat. No. 2,566,957 discloses that di-tert.butoxydiacetoxysilane may be prepared by reacting di-tert.butoxydichlorosilane with acetic acid in the presence of suitable acid acceptors and solvents. This process has the disadvantage that, depending upon the acid acceptor which is employed, it produces as by-products very finely divided amine hydrochlorides which are difficult to filter off or wash out. The yields of target product which can be achieved with this procedure are about 76% of theory and require the use of di-tert.butoxydichlorosilanes a starting material, which is accessible only by a complex process Zhurnal obscej Chimii 27 (1957), pp. 921 to 926, discloses that alkoxyacetoxysilanes can be prepared by reacting alcohols with triacetoxysilane. In this publication it is stated that tertiary alcohols react with tetraacetoxysilane only with difficulty. If tert.butanol is used as the alcohol reactant, the reaction mixture must be warmed to temperatures of 100° to 140° C. in order to obtain tert.butoxyacetoxysilanes. For instance, to prepare di-tert.butoxydiacetoxysilane it was necessary to heat a mixture of tetraacetoxysilane and tert.butanol in a molar ratio of 1:2 at up to 100° C. for 4 hours. Even then, the target product yield obtained by distillation of the reaction mixture was only 48% of theory.

OBJECTS OF THE INVENTION

It is an object of the present invention to provide a process for the preparation of di-tert.butoxydiacetoxysilane which does not employ difficultly accessible starting materials, and in which the starting materials are converted as quantitatively as possible into the target product.

Other objects and advantages of the present invention will become apparent as the description thereof proceeds.

DESCRIPTION OF THE INVENTION

We have discovered that the above object is achieved by reacting tetraacetoxysilane and tert.butanol at temperatures of 0° to 60° C. and subsequently isolating the resulting di-tert.butoxydiacetoxysilane.

A preferred embodiment of the process comprises performing the reaction of tetraacetoxysilane and tert.butanol in the presence of the reaction mixture which results from the preparation of tetraacetoxysilane from silicon tetrachloride and acetic acid.

The sequence in which the reactants react with one another is immaterial for the course of the reaction. The preferred course of reaction comprises allowing the tert.butanol in liquid form to act upon the initially introduced solid tetraacetoxysilane. The end of the reaction can be detected by the fact that the initially heterogeneous system becomes homogeneous. This condition is reached about 30 minutes after completion of the combination of the reactants. In contrast to the process described in the above mentioned publication (Zhurnal obscej Chimii), the reaction, which is known as such, proceeds within a short period of time when it is performed within the temperature range of 0° to 60° C. in accordance with the present invention.

Subsequent heating after the homogeneous reaction solution has formed is not necessary.

The reaction of tetraacetoxysilane with tert.butanol within the temperature range of 0° to 60° C. may also be carried out in the presence of an inert medium Substances of this type, such as aliphatic hydrocarbons, aromatic hydrocarbons or chlorinated hydrocarbons, have no specific effect on the course of the reaction.

The use of aliphatic hydrocarbons as the solvent medium is particularly advisable if the tetraacetoxysilane starting material is the raw reaction product of the reaction of silicon tetrachloride and acetic acid.

Since the reaction is not accompanied by any release of heat, it is possible to combine the reaction partners, tetraacetoxysilane and tert.butanol, without any problems, even in relatively large amounts.

The reaction may be carried out either continuously or batchwise, the latter being preferred. For continuous performance, the alcohol reactant and the tetraacetoxysilane, optionally suspended in an inert liquid medium, are introduced simultaneously, taking into account the stoichiometric requirements, into a suitable reactor such as a tubular reactor. After a given residence time, the reaction product di-tert.butoxydiacetoxysilane, residues of unreacted starting material possibly small amounts of by-products and acetic acid which is also formed, leave the reactor.

The reaction of tetraacetoxysilane with tert.butanol is carried out according to the present invention at temperatures of 0° to 60° C. When these reaction temperatures are used, improved yields of di-tert.butoxydiacetoxysilane are obtained which are up to 100% above the yields of heretofore known methods for the preparation of the target product.

In the reaction of tetraacetoxysilane and tert.butanol within the temperature range of 0° to 60° C., the yields of di-tert.butoxydiacetoxysilane vary only insignificantly, a slight tendency toward reduction in yield being detectable with increasing reaction temperature. For this reason the reaction is preferably carried out in the temperature range of 40° to 60° C. If reaction temperatures above 60° C. are used significant reductions in the yield of di-tert.butoxydiacetoxysilane occur. The lower limit of the operative temperature range according to the present invention is determined by the melting point of tert.butanol, which can be lowered to temperatures of about 0° C. by adding suitable solvents. Thus, it is important that the tert.butanol reactant be available for the reaction in the form of a liquid phase.

The tetraacetoxysilane and tert.butanol reactants are preferably employed in a molar ratio of 1:1.9 to 2.2.

It has proven to be advantageous to react the reaction partners in the molar ratio 1:2. If this molar ratio is chosen, reaction products are obtained which are essentially free from the by-products tert.butoxytriacetoxysilane and tri-tert.butoxyacetoxysilane.

The reaction is carried out at atmospheric pressure. The use of reduced pressure or superatmospheric pressure is possible, but neither has any significant effect on the course of the reaction. The crude products obtained by the method according to the present invention are worked up in conventional manner. Any solvent used for this purpose and the acetic acid formed during the reaction are preferably removed by distillation. Irrespective of the composition of the crude product, the work-up is carried out in vacuo from the outset. Precautions are taken during the entire work-up procedure to ensure that the phase containing the reaction product, di-tert.butoxydiacetoxysilane, is not heated to above 90° C. for any length of time.

After removal of all the low boiling point substances from the raw reaction mixture by distillation, di-tert-.butoxydiacetoxysilane is obtained with a purity which is adequate for many purposes. Certain areas of application may require a somewhat higher product quality, which can be obtained by final distillation in a thin-film evaporator in vacuo in temperatures below 90° C.

The following examples illustrate the present invention and will enable others skilled in the art to understand it more completely. It should be understood, however, that the invention is not limited solely to the particular examples given below.

EXAMPLE 1

1056 g (4 mols) of tetraacetoxysilane were introduced into a 4-liter double-jacketed flask equipped with a reflux condenser, stirrer, dropping funnel and thermometer and heated with a temperature controlled circulating liquid heating device 480 g (8 mols) of tert.butanol were added by way of the dropping funnel over the course of 3 minutes to the initially introduced tetraacetoxysilane, which was kept at a temperature of 23° C. by way of the thermostatically controlled heating device. The reaction went to completion within 30 minutes, which was indicated by the complete disappearance of the tetraacetoxysilane. Analysis of the contents of the flask by gas-chromatography (GC) indicated the presence of the target product di-tert.butoxydiacetoxysilane in addition to acetic acid. The crude product was transferred into a distillation apparatus which consisted of a double-jacketed distillation still connected to a thermostatically controlled circulating liquid heating device, an inserted thermometer, and a distillation attachment which was connected to a vacuum pump via a cold trap. The crude product was freed from all of the acetic acid within 2 hours at a sump temperature of up to a maximum of 85° C. A clear, virtually colorless liquid (1153 g) with a purity (GC) of 97% remained. Further purification of the still product by distillation in a glass laboratory thin-film evaporator in vacuo gave 1131 g of a distillate having a purity (GC) of 98% and a residue weighing 22 g.

EXAMPLE 2 (COMPARATIVE EXAMPLE)

Example 1 was repeated, but a reaction temperature of 115° C. was used.

Analysis of the crude reaction product by gas-chromatography indicated the presence of a target product in addition to acetic acid. In addition, the presence of an increased amount of siloxanes was detected. After removal of the low-boiling-point components by distillation, 1096 g of yellow residue containing 43.7% of di-tert.butoxydiacetoxysilane remained in the distillation still. Further work-up by distillation gave 465 g of distillate and 598 g of residue.

EXAMPLE 3 (COMPARATIVE EXAMPLE)

Example 2 was repeated, but 2000 ml of octane were added to the initially introduced amount of tetraacetoxysilane.

After removal of the octane, the acetic acid and low-boiling-point components by distillation, 1096 g of a yellow product containing 59.7% of di-tert.butoxydiacetoxysilane (GC) remained in the distillation still. Further work-up of this still residue by distillation gave 658 g of distillate and 434 g of residue.

EXAMPLE 4

1050 g of acetic acid anhydride were introduced into a reaction flask equipped with a distillation attachment. 350 g of silicon tetrachloride were metered into the flask over the course of 5 minutes at 25° C. The precipitated tetraacetoxysilane was freed from acetyl chloride and excess acetic anhydride by distillation. 350 g of tert.butanol were added to the dry tetraacetoxysilane distillation residue at room temperature. The di-tert-.butoxydiacetoxysilane/acetic acid mixture formed thereby was freed from acetic acid by vacuum distillation, and was further purified by distillation in a thin-film evaporator. 578 g of colorless di-tert.butoxydiacetoxysilane with a purity (GC) of 98% were obtained.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In the method of preparing di-tert.butoxydiacetoxysilane by reacting tetraacetoxysilane with tert.butanol, the improvement which comprises performing the reaction at a temperature of 0° to 60° C., and isolating the resulting di-tert.butoxydiacetoxysilane product.

2. The method of claim 1, wherein the tetraacetoxysilane reactant is the unrefined reaction product of the reaction of silicon tetrachloride with acetic acid.

3. The method of claim 1, wherein the reaction is carried out at a temperature from 40° to 60° C.

4. The method of claim 1, wherein the reaction is performed in the presence of an inert aliphatic hydrocarbon medium.

* * * * *